United States Patent
Lisman

(10) Patent No.: US 11,650,166 B2
(45) Date of Patent: May 16, 2023

(54) METHOD FOR EVALUATION OF GLASS CONTAINER

(71) Applicant: NIPRO CORPORATION, Osaka (JP)

(72) Inventor: Dave Lisman, Millville, NJ (US)

(73) Assignee: NIPRO CORPORATION, Osaka (JP)

( * ) Notice: Subject to any disclaimer, the term of this patent is extended or adjusted under 35 U.S.C. 154(b) by 0 days.

(21) Appl. No.: 16/617,553

(22) PCT Filed: May 30, 2018

(86) PCT No.: PCT/JP2018/020801
§ 371 (c)(1),
(2) Date: Nov. 27, 2019

(87) PCT Pub. No.: WO2018/221605
PCT Pub. Date: Dec. 6, 2018

(65) Prior Publication Data
US 2020/0141878 A1   May 7, 2020

Related U.S. Application Data

(60) Provisional application No. 62/512,778, filed on May 31, 2017.

(51) Int. Cl.
*G01N 21/88* (2006.01)
*G01N 21/90* (2006.01)
(Continued)

(52) U.S. Cl.
CPC ......... *G01N 21/8851* (2013.01); *G01N 21/90* (2013.01); *G01N 21/95* (2013.01);
(Continued)

(58) Field of Classification Search
CPC ........... G01N 21/8851; G01N 21/8914; G01N 21/892; G01N 21/90; G01N 21/9018; G01N 2021/945; G01N 21/95
See application file for complete search history.

(56) References Cited

U.S. PATENT DOCUMENTS 4,428,674 A * 1/1984 Giebel .................. G01N 21/90
250/223 B
4,691,231 A * 9/1987 Fitzmorris ............ B07C 5/3408
209/522

(Continued)

FOREIGN PATENT DOCUMENTS

DE   102014002582 A1 * 8/2015 ........... G06T 7/0004
EP   1 923 359           5/2008
(Continued)

OTHER PUBLICATIONS

Zai-Qing Wen, et al., Nondestructive Detection or Glass Vial Inner Surface Morphology with Differential Interference Contrast Microscopy,Journal of Pharmaceutical Sciences, vol. 101, Issue 4, 2012, p. 1378-1384, ISSN 0022-3549,https://doi.org/10.1002/jps.23048. (Year: 2012).*

(Continued)

*Primary Examiner* — Michael Robert Cammarata
(74) *Attorney, Agent, or Firm* — Wenderoth, Lind & Ponack, L.L.P.

(57) ABSTRACT

The present invention provides a method for evaluating a processing deterioration level of a medical glass container, including (a) a step of imaging a surface of a medical glass container molded from a borosilicate glass tube to obtain an image, and (b) a step of analyzing a contrast of the image. The method is particularly useful to evaluate the amount of alkali substances which are deposited on the inner side surface of a medical glass container.

14 Claims, 8 Drawing Sheets

(51) Int. Cl.
  *G01N 21/95* (2006.01)
  *G01N 33/38* (2006.01)
  *A61J 1/06* (2006.01)
(52) U.S. Cl.
  CPC ............. *G01N 33/386* (2013.01); *A61J 1/065* (2013.01); *G01N 2021/8887* (2013.01)

(56) References Cited

U.S. PATENT DOCUMENTS

| | | | | |
|---|---|---|---|---|
| 6,271,825 | B1* | 8/2001 | Greene | H04N 9/12 345/694 |
| 6,597,804 | B1* | 7/2003 | Heuft | G01N 21/90 348/127 |
| 6,999,625 | B1* | 2/2006 | Nelson | G06T 7/0012 382/103 |
| 8,522,575 | B2 | 9/2013 | Wada | |
| 8,820,119 | B2* | 9/2014 | Kuwabara | C03B 23/0093 65/65 |
| 9,010,150 | B2 | 4/2015 | Kuwabara et al. | |
| 2005/0168732 | A1* | 8/2005 | Miller | G01N 21/94 356/239.8 |
| 2006/0181700 | A1* | 8/2006 | Andrews | G01N 21/474 356/237.2 |
| 2006/0203468 | A1* | 9/2006 | Beeson | H01L 33/60 257/E33.072 |
| 2006/0210142 | A1* | 9/2006 | Oguni | G01N 21/95692 382/145 |
| 2006/0211071 | A1* | 9/2006 | Andre | G01N 33/86 435/13 |
| 2008/0032429 | A1* | 2/2008 | Chen | G01N 21/8851 438/14 |
| 2009/0099000 | A1 | 4/2009 | Kuwabara et al. | |
| 2011/0255745 | A1* | 10/2011 | Hodder | G06T 7/0002 382/103 |
| 2013/0208978 | A1* | 8/2013 | Ribnick | G06T 7/0004 382/159 |
| 2013/0233021 | A1 | 9/2013 | Kuwabara et al. | |
| 2013/0233022 | A1 | 9/2013 | Kuwabara et al. | |
| 2013/0283860 | A1 | 10/2013 | Kuwabara et al. | |
| 2013/0316934 | A1 | 11/2013 | Matayoshi et al. | |
| 2014/0001076 | A1* | 1/2014 | Fadeev | C03C 17/3405 206/524.3 |
| 2014/0034544 | A1* | 2/2014 | Chang | B65D 23/0814 206/524.3 |
| 2014/0177932 | A1* | 6/2014 | Milne | G01N 21/8851 382/128 |
| 2014/0240694 | A1* | 8/2014 | Scheumann | G01N 21/91 356/36 |
| 2014/0341891 | A1* | 11/2014 | Weeks | A61K 31/727 424/133.1 |
| 2014/0362207 | A1* | 12/2014 | Leconte | G01N 21/9045 348/86 |
| 2016/0095980 | A1* | 4/2016 | Denina | G01N 21/954 356/241.1 |
| 2016/0171705 | A1* | 6/2016 | Bendall | G06T 7/001 382/103 |
| 2016/0251260 | A1* | 9/2016 | Bayne | B65D 1/09 428/34.7 |
| 2017/0054905 | A1* | 2/2017 | Iwasaki | H04N 5/23238 |
| 2017/0200406 | A1* | 7/2017 | Lin | G09G 3/2003 |
| 2017/0327404 | A1 | 11/2017 | Kuwabara et al. | |
| 2017/0327405 | A1 | 11/2017 | Kuwabara et al. | |
| 2018/0105449 | A1 | 4/2018 | Wada et al. | |
| 2018/0111868 | A1 | 4/2018 | Moriuchi et al. | |
| 2018/0134603 | A1 | 5/2018 | Inoue | |
| 2019/0164269 | A1* | 5/2019 | Klager | G06T 7/97 |
| 2019/0336358 | A1* | 11/2019 | Goda | A61F 13/53 |

FOREIGN PATENT DOCUMENTS

| | | | | |
|---|---|---|---|---|
| JP | 59-79804 | | 5/1984 | |
| JP | 10-9836 | | 1/1998 | |
| JP | 2000155100 | A * | 6/2000 | |
| JP | 3963408 | B2 * | 8/2007 | |
| JP | 6358351 | B1 * | 7/2018 | ......... G01N 21/8851 |
| WO | WO-2016095318 | A1 * | 6/2016 | ............ G01N 21/88 |
| WO | 2016/163426 | | 10/2016 | |
| WO | 2016/171197 | | 10/2016 | |
| WO | 2016/171214 | | 10/2016 | |
| WO | WO-2017204766 | A2 * | 11/2017 | ......... G01N 21/9036 |

OTHER PUBLICATIONS

Z. Yang and J. Bai, "Vial bottle mouth defect detection based on machine vision," 2015 IEEE International Conference on Information and Automation, 2015, pp. 2638-2642, doi: 10.1109/ICInfA.2015.7279730. (Year: 2015).*

Ennis, Richard D et al. "Glass Vials for Small Volume Parenterals: Influence of Drug and Manufacturing Processes on Glass Delamination." Pharmaceutical development and technology 6.3 (2001): 393-405. (Year: 2001).*

R. E. Levin, "Luminance—A Tutorial Paper," in Journal of the SMPTE, vol. 77, No. 10, pp. 1005-1011, Oct. 1968, doi: 10.5594/J13629. (Year: 1968).*

International Search Report (ISR) dated Aug. 21, 2018 in International (PCT) Application No. PCT/JP2018/020801.

Office Action dated Jan. 10, 2022 in Indian Patent Application No. 201917048458, with English translation.

* cited by examiner

Prior Art

[Fig. 7]

Fig. 9A
Manufacturing a glass container and imaging a portion of a surface of the glass container
Converting the image into a grayscale digital image
Fig. 9B
Manufacturing a glass container
imaging a portion of a surface of the glass container
Converting the image into a grayscale digital image

METHOD FOR EVALUATION OF GLASS CONTAINER

BACKGROUND OF THE INVENTION

The invention is directed to a method for evaluating the processing deterioration level of a glass container such as a medical glass container molded from a borosilicate glass. In particular, the method is useful for evaluating the amount of alkali deposits on the inner side surface of a glass container such as a medicinal glass container. The invention is also directed to a system as well as a device used for such method.

There are known methods for making a medical glass container such as a medical vial. For example, see U.S. Pat. Nos. 8,522,575; 8,820,119; 9,010,150; WO2016/163426; and WO2016/171197, the contents of which are hereby incorporated by reference.

In order to manufacture a medical vial from a borosilicate glass tube, a mouth portion of a vial and a bottom portion thereof are molded in the glass tube by heating the glass tube with a high temperature flame. In automated systems, the medical vial is formed in an inverted (upside down) manner. Thus the glass tube is held in a vertical direction, the mouth portion of the medical vial is formed at the bottom of the glass tube, and the bottom portion of the medical vial is formed above the mouth portion of the medical vial along the vertical axis. In the step of molding the bottom portion from the glass tube, an alkali component volatilized from the glass tube due to heating the glass tube condenses particularly on an inner surface near the bottom portion to generate a deterioration region as alkali deposits. The alkali component is eluted from such a deterioration region into a medicine or the like in the vial when the medicine is stored in the medical vial.

In recent years, in addition to the problem of elution of an alkali component, it has been seen as a problem that silica particles or flakes peeled off an inner surface of a vial are mixed with a medicine in the vial. With respect to this problem, the United States Pharmacopeia (USP) <660> and European Pharmacopeia (EP) 3.2.1, ISO4802-1, or ISO4802-2 defines elution criteria of an alkali component. In addition, Chapter <1660> entitled "inner surface durability evaluation of glass container" in the United States Pharmacopoeia (USP) describes a vial sorting method for evaluating the amount of silica ($SiO_2$) eluted by heating a glass container at 121° C. for two hours using a high ionic strength solution of a 0.9% KCl aqueous solution (pH 8.0).

As a test method for evaluating an interlayer peeling tendency in a glass packaging method, a test method requiring a plurality of steps, for example, forming a corrosion region by exposure to a vapor atmosphere or making a corrosion region visible by dyeing is known (see for example WO2016/171214). However, these test methods based on the elution criteria are complicated and require time for a quality guarantee test disadvantageously. In addition, these test methods cannot be performed on a vial manufacturing line.

On the other hand, the following is known. That is, by performing fire blasting of oxygen-flammable gas flame with a point burner with respect to a deterioration region generated on an inner surface of a vial molded from a borosilicate glass tube while the vial is rotated, the deterioration region is removed, the elution of an alkali component is thereby reduced, and the elution of silica is also reduced (see for example U.S. Pat. No. 8,820,119; WO 2016/163426; and WO 2016/171214).

A deterioration region includes a deposit obtained by condensation of many small droplets containing an alkali ($Na_2O$ or the like) exuded or volatized from glass on an inner surface of the vial. Therefore, an uneven, droplet-like pattern on the inner surface of the glass can be observed. For example, the deposit can be visually observed by imaging the deposit with a scanning electron microscope (SEM). However, this visual observation method serves only as a qualitative measure.

SUMMARY OF THE INVENTION

An object of the present invention is to provide an evaluation method, an evaluation system and also an evaluation device of a surface of a glass container such as a medical glass container molded from a borosilicate glass tube.

In the first aspect, the present invention provides a method for evaluating a glass container, particularly evaluating a level of deterioration and potential of silica peeling off of a glass container such as a medical glass container molded from a borosilicate glass tube, comprising:
 (a) a step of imaging at least a portion of a surface of the glass container to obtain its image, and
 (b) a step of analyzing a contrast of the image.

In the second aspect, the present invention provides a system for evaluating a glass container, particularly evaluating a level of deterioration and potential of silica peeling off of a glass container such as a medical glass container molded from a borosilicate glass tube, comprising:
 (A) an imager which images at least a portion of a surface of the glass container to obtain its image, and
 (B) an analyzer member which analyzes a contrast of the image.

In the third aspect, the present invention provides a device for evaluating a glass container, particularly evaluating a level of deterioration and potential of silica peeling off of a glass container such as a medical glass container molded from a borosilicate glass tube, comprising:
 (i) an imaging member which images at least a portion of a surface of the glass container to obtain its image, and
 (ii) an analyzing member which analyzes a contrast of the image.

In the invention, evaluating the level of deterioration and potential of silica peeling off of a glass container means determining whether or not the container in question has a quality which is similar to or better than that of a container of the same kind having successfully been subjected to the fire blasting. That is, such evaluation is checking whether the container in question substantially has a level of no problem about the deterioration and potential of silica peeling off in view of application of the container.

According to the present invention, a quality of the glass container, particularly the medical glass container such as a vial or an ampule, in view of the deterioration and potential of peeling off silica level of the surface of the glass container can be evaluated without performing a complicated alkali or silica elution test.

BRIEF DESCRIPTION OF DRAWINGS

FIG. 9A and FIG. 9B depict the step of imaging may be performed during (FIG. 9A) or after (FIG. 9B) manufacture of the glass container in the method of the invention.

DETAILED DESCRIPTION OF THE INVENTION

The present invention will hereinafter be explained in detail by describing an embodiment of a method of evaluating a glass container. However, it is to be understood that the specific features explained below are simply exemplary, and it should be clear to a person of ordinary skill in the art that the method can be modified within the scope of the claims.

It is to be noted that the method of the invention will mainly be explained hereinafter, but such explanations are also applicable to the system and the device of the invention.

The method of the invention is directed to evaluation of a glass container such as a medical glass container molded from a borosilicate glass tube. The glass container molded from a borosilicate glass tube is not particularly limited so long as it is a container having a bottom formed from a borosilicate glass tube. The medical glass container is preferably a vial or an ampule.

Figure 1:
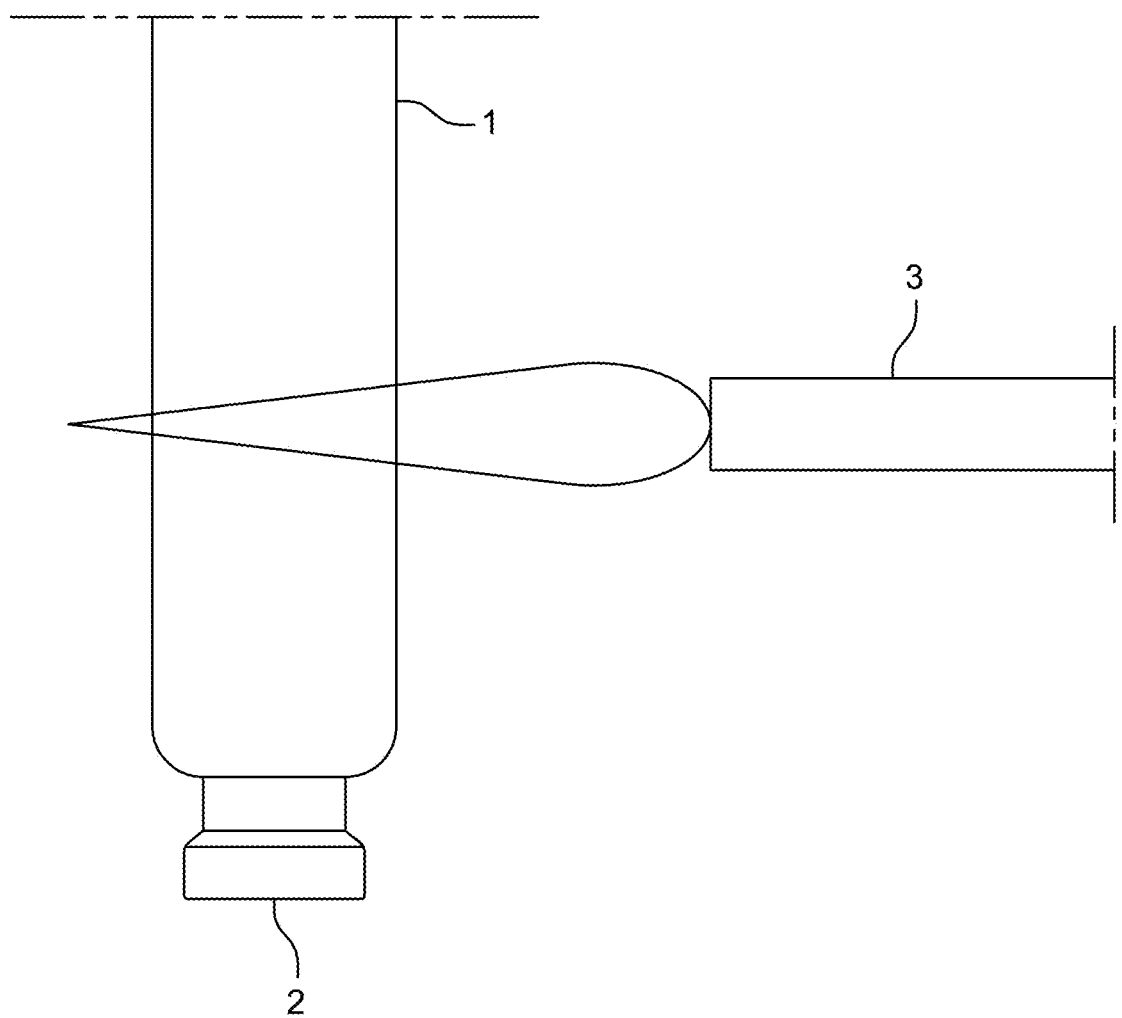
FIG. 1 is an illustration of a process for forming a medical glass container by heating a glass tube with a flame.
Figure 2:
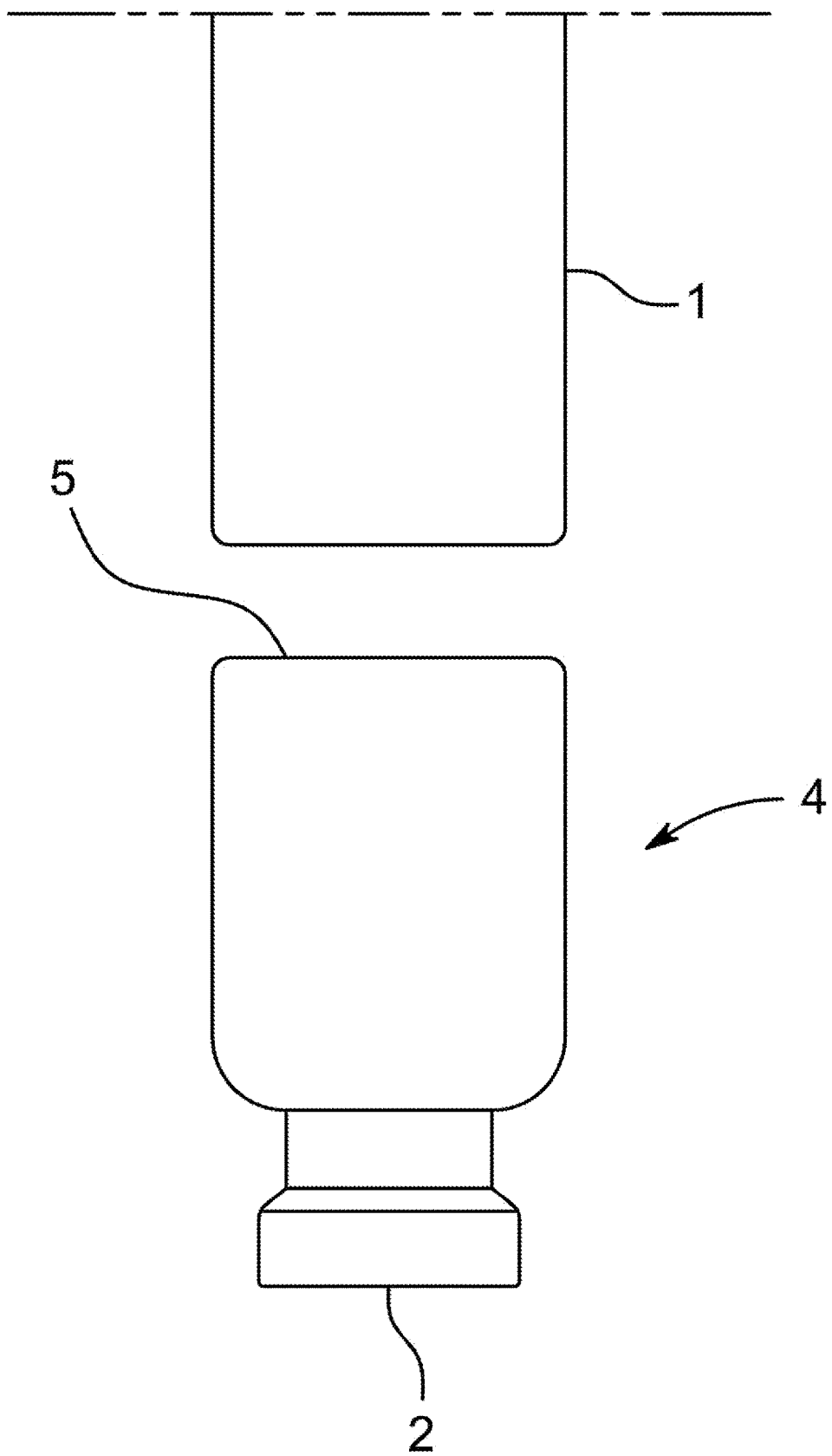
FIG. 2 is an illustration of a medical glass container formed by the process shown in FIG. 1, which container has just been separated from the glass tube.

FIG. 1 is an illustration of a process for forming a medical glass container by heating a glass tube 1 having a formed mouth portion 2 using a flame 3. FIG. 2 is an illustration of a medical glass container 4 having a formed mouth portion 2 and bottom portion 5 formed by the process shown in FIG. 1 so as to separate the container 4 from the glass tube 1 and form the bottom portion 5.

The step of imaging a surface of a medical glass container molded from a borosilicate glass tube is performed by imaging at least a portion of surface of the medical glass container. Specifically, the surface may be a side surface, a heel (or lower end portion) surface, an inner side surface, an outer side surface, etc. Preferably the step of imaging is performed by imaging a side surface, particularly, a side surface close to the bottom of the medical glass container. More preferably, the step of imaging is performed by imaging an inner side surface of the medical glass container. More preferably, the step of imaging the surface is performed by imaging an inner side surface of the medical glass container which side surface is about 3 to 5 mm from the heel of the container.

The step of imaging the surface may be performed during or after manufacture of the glass container such as a medical glass container. Specifically, the imaging may be performed preferably at the end of the manufacture in the manufacturing line. Alternatively, the imaging may be performed after the manufacture, for example immediately prior to filling the medical glass container with the medicinal composition. During the manufacture of the medical glass container, the heel of the medical glass container is formed, and then the glass container is annealed. The step of imaging the surface may be performed before or after annealing of the medical glass container. The step of imaging may also be performed after fire blasting of the inside of the medical glass container.

The imaging may be performed using any conventional imaging device as an imager or an imaging member in the step (a). The imaging device may produce a color image or grayscale image. Generally, the imaging device produces a digital image comprising a plurality of image pixels each of which has a brightness value. If the imaging device produces a color image, preferably the color image is converted to a grayscale image.

Preferably, the imaging is performed using an optical microscope or a scanning electron microscope (SEM). An optical digital microscope is more preferably used. For example, as the optical microscope, a digital microscope VHX-2000 manufactured by Keyence Corporation can be used. The imaging may be performed at any suitable surface magnification, for example 50× to 1000×. Preferably the step of imaging is performed with an optical digital microscope using a surface magnification of 200× to 500×.

As explained above, the obtained image is analyzed with regard to its contrast in the step (b) while using an analyzer or an analyzing member, which is generally a PC installed with a data processing (or analyzing) software.

When the obtained image is not a grayscale image, it may preferably be converted into a grayscale image using a conventional image processing software. Then, grayscale image is analyzed by processing it with regard to its contrast. It is of course possible to analyze the image without converting into the grayscale image. Preferably the image processing is performed by an arithmetic means. For example, it is possible to use an image analysis software "Image J" (NIH), or an image processing function which is included in the digital microscope, such as the image processing function included in the digital microscope VHX-2000.

Figure 3:
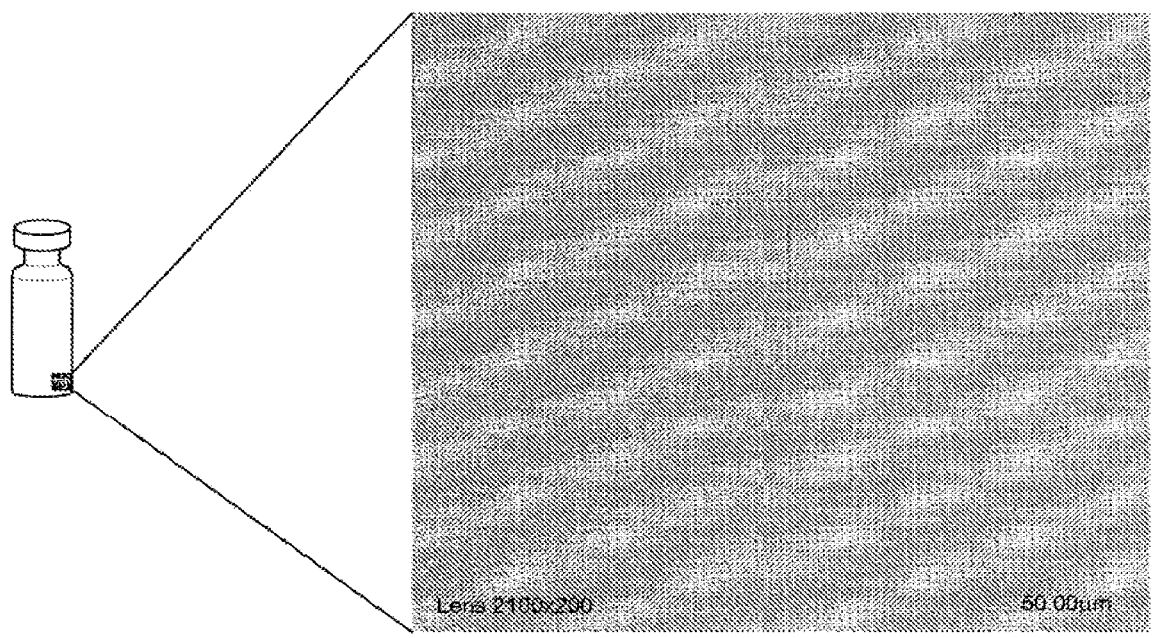
FIG. 3 is an illustration of a medical glass container which is imaged by an optical microscope.
Figure 4:
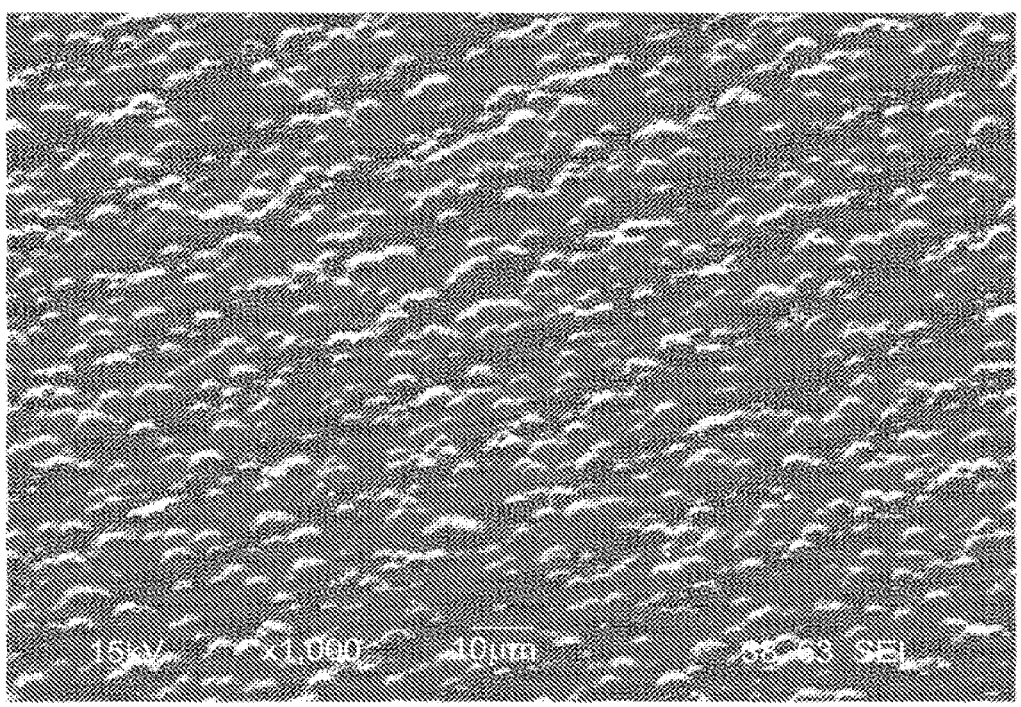
FIG. 4 is an electron microscope photograph of a surface of a medical glass container which has not been subjected to fire blasting.
Figure 5:
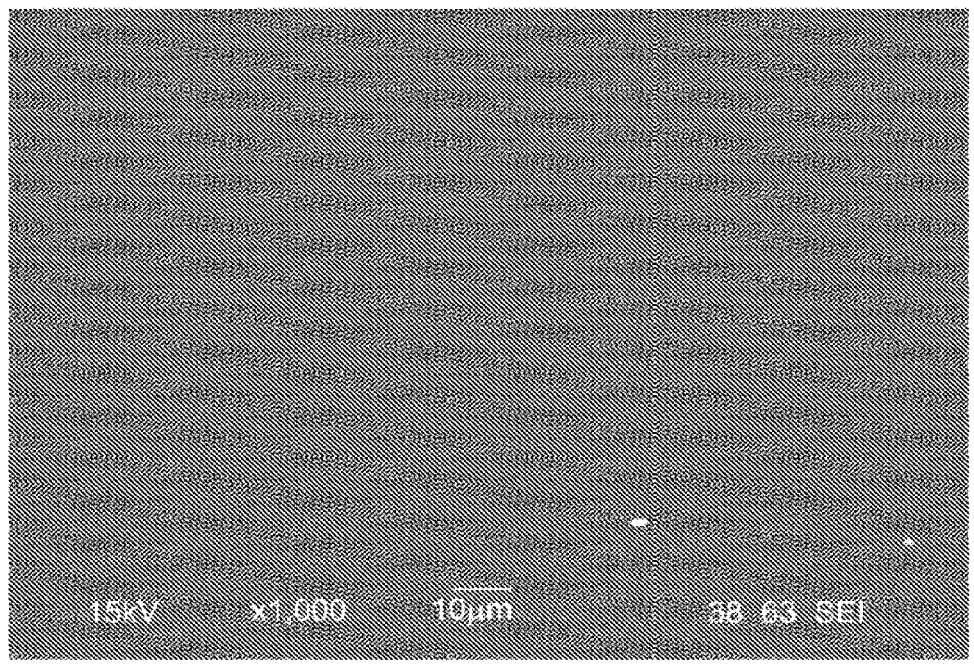
FIG. 5 is an electron microscope photograph of a surface of a medicinal glass container having substantially no deteriorated region which container has been subjected to fire blasting.

FIG. 3 is an illustration of a medical glass container which is imaged by an optical microscope. FIG. 4 is an electron microscope photograph of a surface of a medicinal glass container which has not been subjected to fire blasting. The photograph shows that there is a deteriorated region of the medical glass container due to processing of the glass tube, which region has an uneven surface deposit pattern resulting from alkali-containing volatiles. On the other hand, FIG. 5 is an electron microscope photograph of a surface of a medicinal glass container which has been subjected to fire blasting. This photograph shows that the region corresponding to the deteriorated region due to processing has no uneven surface deposit pattern. It is seen from the photographs that the deteriorated region due to processing was removed by fire blasting.

The step of analyzing a contrast of the obtained image such as a grayscale image is not particularly limited. As described above, the digital image such as a grayscale digital image comprises a plurality of image pixels, wherein each image pixel is assigned a brightness value.

In other embodiment, the step of analyzing a contrast of an image such as a grayscale image may be carried out by analyzing a brightness value distribution of a pixel. As described above, a grayscale digital image comprises a plurality of image pixels, wherein each image pixel is assigned a brightness value. The step of analyzing the contrast of the image is performed by analyzing the brightness values of the plurality of image pixels. The brightness values of the plurality of image pixels are preferably used to create a brightness value distribution profile which can be displayed as a brightness value distribution histogram.

A large difference in the brightness value distribution (i.e. a broad brightness value distribution) indicates presence of multiple deposits. A small difference in the brightness value distribution (i.e. a sharp or narrow brightness value distribution) means that a deposit has almost been removed by fire blasting, or lessened by other means.

From the brightness value distribution profile, it has been determined according to experimental data that a deposit and potential of peeling off silica has not been sufficiently removed, when a histogram extraction is performed by setting a brightness value range from 0 (darkest value) to 255 (brightest value), for example, and a difference between a maximum value of brightness value and a minimum value thereof is from 50 to 140.

From the brightness distribution profile, it has been determined according to experimental data that deposits and potential of peeling off silica has been sufficiently removed, when a histogram extraction is performed by setting a brightness range from 0 to 255, for example, and a difference between a maximum value and a minimum value is from 10 to 20.

Thus the brightness value distribution profile is correlated to the quality of the glass container such as the medical glass container, that is, the level of the processing deterioration and the potential of peeling off silica of the glass container. Preferably, the brightness value distribution profile is correlated to an amount of alkaline deposits and potential of peeling off silica on the inner side surface of the glass container.

When the glass container has been evaluated using the inventive method, a determination can be made whether or not the glass container satisfies a predetermined standard for the processing deterioration and peeling off silica level. For example, the values of the brightness value distribution profile may be compared with predetermined values to determine whether or not the imaged medical glass container is within the range of acceptable values, or exceeds acceptable values. The predetermined values may correspond to the standards defined by ISO4802 or other government standard which defines the maximum values for alkaline deposits or other deterioration substances such as the potential of peeling off silica on the inner surface of a glass container such as a medical glass container. The predetermined values are preferably 10 to 50% of the standards defined by ISO4802 or other government standard.

Specifically, an image of a glass container to be evaluated is first obtained, and the image is then analyzed to have a brightness value profile, followed by obtaining a difference between a maximum brightness value and a minimum brightness value from the brightness value profile. Thus obtained difference is compared with a predetermined standard difference to determine whether or not the obtained difference is equal to or smaller than the predetermined standard difference. If yes, the evaluated container has a quality which is equal to or better than a standard glass container. If not, the evaluated container has a quality which is worse than the standard container. It is noted that the predetermined standard difference should have been obtained beforehand as to the standard glass container which satisfies a deterioration and potential of peeling off silica level of the glass container required by a law, regulation, standard such as ISO4802 or other government standard. It is further better that the predetermined standard difference is smaller, preferably 30% smaller, more preferably 50% smaller, most preferably 70% smaller than the difference of the glass container which satisfies the required deterioration and silica peeling off level of the glass container.

When the glass container such as a medical glass container, or a sample from a batch of medical glass containers, is determined to have an acceptable level of processing deterioration, such as alkaline deposits and potential of silica peeling off, the glass container such as a medical glass container may be subjected to further processing, such as sterilization, packaging, and/or filling with the medicinal composition.

EXAMPLES

A vial which had not been subjected to fire blasting and a vial which had been subjected to fire blasting were subjected the method of this invention. The side surface of the vial was imaged using an optical microscope (digital microscope VHX-2000 manufactured by Keyence Corporation) as shown in FIG. 3. The image was analyzed using image analysis software (Image J (NIH)).

Example 1

Figure 6:
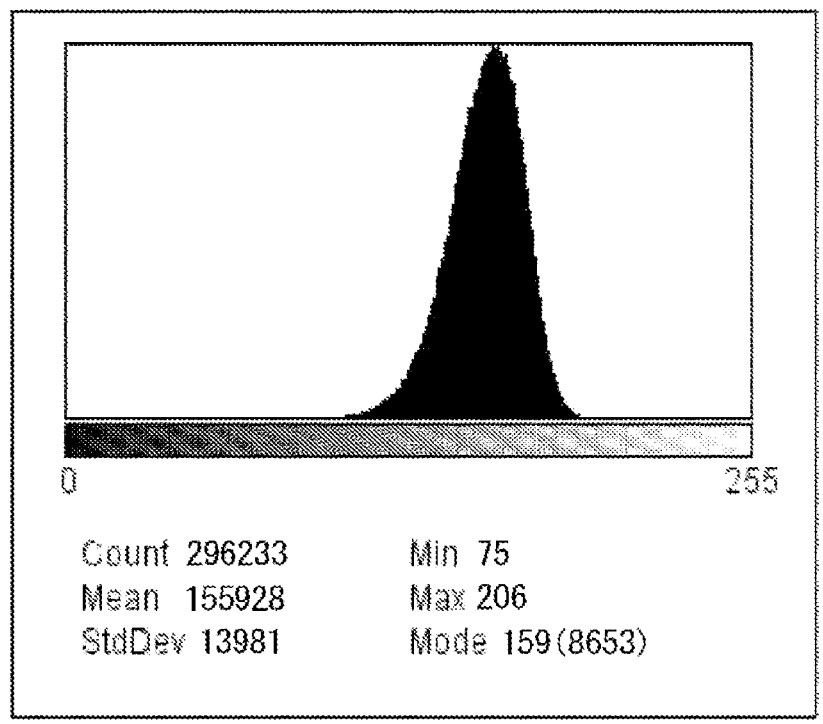
FIG. 6 is a brightness distribution profile of a grayscale image of a surface of a medicinal glass container which has not been subjected to fire blasting.

FIG. 6 shows a brightness value distribution histogram of the grayscale image pixels of the vial which had not been subjected to fire blasting. The brightness value distribution histogram shows a difference in brightness value is as large as 131 (=206 minus 75). This wide variance in the minimum and maximum values of the brightness value of the pixel images correlates with the presence of substantial deposits and high potential of peeling off silica on the inside of the medical glass container.

In FIG. 6, the y-axis of the brightness value distribution histogram is the "Count of pixels by color". The x-axis of the brightness distribution value profile is the "Black/white color scale divisions".

Example 2

Figure 7:
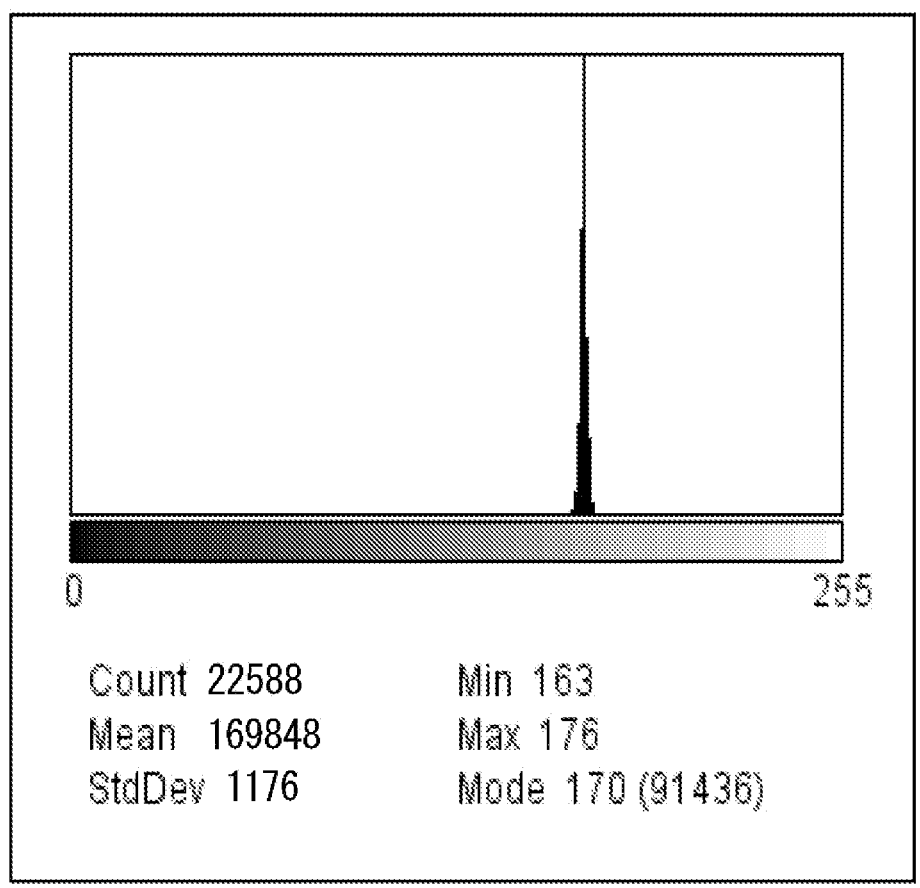
FIG. 7 is a brightness distribution profile of a grayscale image of a surface of a medicinal glass container which has been subjected to fire blasting.
Figure 8:
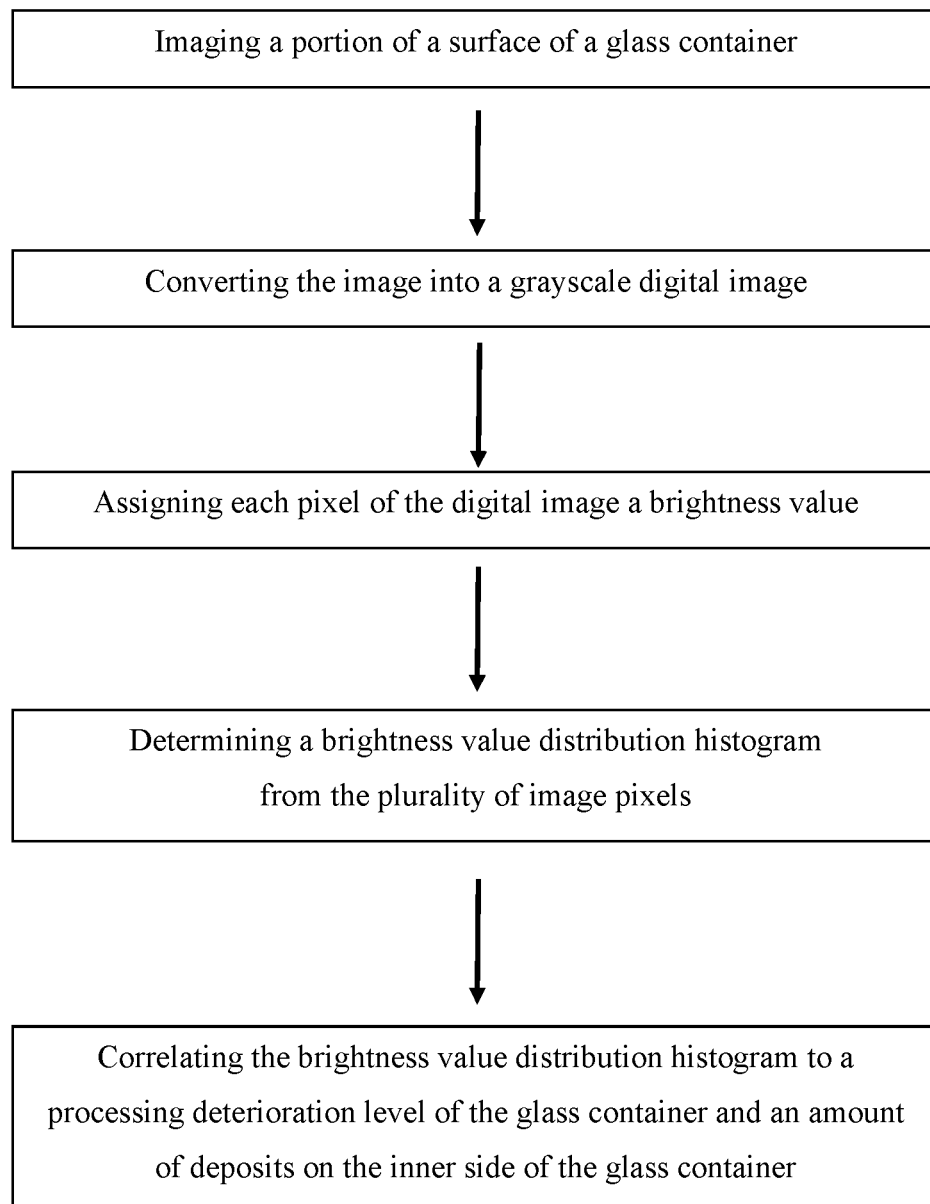
FIG. 8 is a flow chart of the method according to the first aspect of the invention.
Figure 10A:
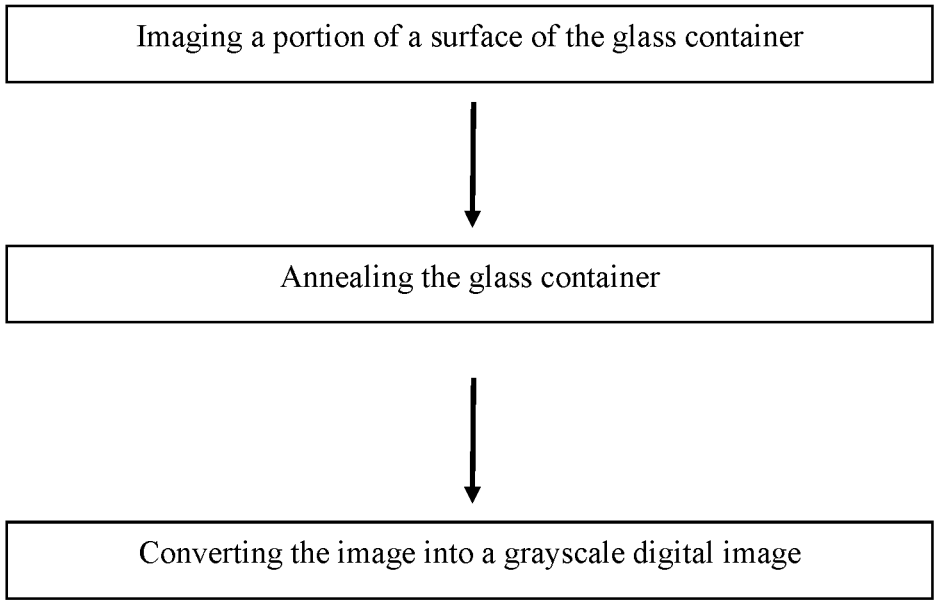
FIG. 10A and FIG. 10B depict the step of imaging may be performed before (FIG. 10A) or after (FIG. 10B) annealing the glass container in the method of the invention.
Figure 10B:
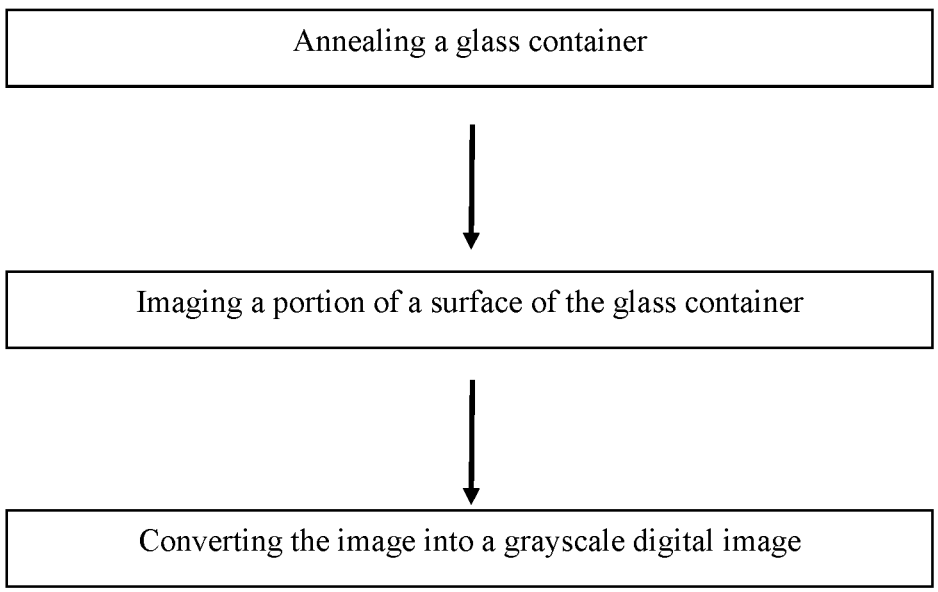

FIG. 7 shows a brightness value distribution histogram of the grayscale image pixels of the vial which had been subjected to fire blasting. The brightness value distribution histogram shows a difference in brightness value is as small as 13 (=176 minus 163). This narrow variance in the minimum and maximum values of the brightness of the pixel images correlates with the presence of insubstantial deposits and no or low potential of peeling off silica on the medical glass container.

In FIG. 7, the y-axis of the brightness value distribution profile is the "Count of pixels by color". The x-axis of the brightness distribution profile is the "Black/white color scale divisions".

Reference Example 1

A vial which had not been subjected to fire blasting and a vial which had been subjected to fire blasting were subjected to an alkali elution test. As a result, the amount of alkali elution of the vial which had been subjected to fire blasting was extremely small in comparison to the amount of alkali elution of the vial which had not been subjected to fire blasting.

The present invention makes it possible to evaluate a processing deterioration level easily. Therefore, the present invention is useful in a rapid quality test of a vial. The present invention can make the number of test samples several times that in a conventional test method.

The invention claimed is:

1. A method for evaluating a level of deterioration and silica peeling off on an inner side surface of a glass container molded from a borosilicate glass tube, comprising:
   (a) a step of imaging at least a portion of a surface of the glass container to obtain its image, and
   (b) a step of analyzing a contrast of the image,
   wherein the step of imaging the portion of the surface is performed by imaging an outer side surface from the outside of the glass container,
   wherein the step of analyzing comprises determining a brightness value distribution histogram from a plurality of image pixels, wherein each image pixel is assigned a brightness value, calculating a difference between a maximum brightness value and a minimum brightness value from the histogram, and comparing the difference with a predetermined standard difference, and
   wherein a deposit and potential peeling off of silica has not been sufficiently removed when the calculated difference between the maximum brightness value and the minimum brightness value from the histogram is between 50 and 140, the deposit and potential peeling off of silica has been sufficiently removed when the calculated difference between the maximum brightness value and the minimum brightness value from the histogram is between 10 and 20, and the brightness value ranges from 0 to 255.

2. The method according to claim 1, wherein the step of imaging is performed with an optical microscope or a scanning electron microscope.

3. The method according to claim 1, wherein the step of imaging is performed with a digital optical microscope.

4. The method according to claim 1, wherein the step of imaging is performed with a digital optical microscope using a surface magnification of 200× to 500×.

5. The method according to claim 1, wherein the outer side surface is 3 to 5 mm from a heel of the container.

6. The method according to claim 1, wherein the step of imaging the portion of the surface is performed during or after manufacture of the glass container.

7. The method according to claim 1, wherein the step of imaging the portion of the surface is performed before or after annealing of the glass container.

8. The method according to claim 1, wherein the image is a grayscale digital image.

9. The method according to claim 1, wherein the image is a color or grayscale image which is converted into a grayscale digital image.

10. The method according to claim 1, wherein the image is a color or grayscale image which is converted into a grayscale digital image by an arithmetic means using computer software.

11. The method according to claim 1, wherein the step of analyzing a contrast of the image is performed using computer software.

12. The method according to claim 1, wherein the image is a grayscale digital image, and the step of analyzing the contrast of the image is performed using computer software.

13. The method according to claim 1, wherein the brightness value distribution histogram is correlated to a processing deterioration level of the glass container.

14. The method according to claim 1, wherein the brightness distribution histogram is correlated to an amount of alkaline deposits on the inner side surface of the glass container.

* * * * *